United States Patent
Hollopeter et al.

(10) Patent No.: US 10,603,132 B2
(45) Date of Patent: Mar. 31, 2020

(54) LIGHTHEAD IDENTIFICATION SYSTEM FOR LIGHTHEAD CONTROL

(71) Applicant: American Sterilizer Company, Mentor, OH (US)

(72) Inventors: Michael Hollopeter, Kirtland, OH (US); Damon Jurkiewicz, Cleveland, OH (US); James A. Petrucci, Chesterland, OH (US); Lance C. Bellows, Painesville, OH (US)

(73) Assignee: American Sterilizer Company, Mentor, OH (US)

( * ) Notice: Subject to any disclaimer, the term of this patent is extended or adjusted under 35 U.S.C. 154(b) by 245 days.

(21) Appl. No.: 15/794,106

(22) Filed: Oct. 26, 2017

(65) Prior Publication Data

US 2018/0116754 A1    May 3, 2018

Related U.S. Application Data

(60) Provisional application No. 62/415,545, filed on Nov. 1, 2016.

(51) Int. Cl.

| F21V 21/04 | (2006.01) |
|---|---|
| A61B 90/30 | (2016.01) |
| H05B 37/02 | (2006.01) |
| F21S 8/04 | (2006.01) |
| F21V 21/15 | (2006.01) |
| F21W 131/205 | (2006.01) |
| F21V 23/04 | (2006.01) |

(52) U.S. Cl.
CPC ............. *A61B 90/30* (2016.02); *F21S 8/046* (2013.01); *F21V 21/04* (2013.01); *F21V 21/15* (2013.01); *H05B 37/0227* (2013.01); *H05B 37/0272* (2013.01); *A61B 2090/308* (2016.02); *A61B 2090/309* (2016.02); *F21V 23/0435* (2013.01); *F21W 2131/205* (2013.01)

(58) Field of Classification Search
CPC .............. A61B 90/30; A61B 2090/308; A61B 2090/309; F21S 8/046; F21V 21/04; F21V 21/15; F21V 23/0435; H05B 37/0227; H05B 37/0272; F21W 2131/205
See application file for complete search history.

(56) References Cited

U.S. PATENT DOCUMENTS

| 3,910,276 A | 10/1975 | Polanyi et al. |
| 4,761,000 A * | 8/1988 | Fisher .................... A61G 13/02 5/600 |
| 6,160,582 A | 12/2000 | Hill |
| 6,464,383 B1 | 10/2002 | Northington et al. |
| 6,513,962 B1 | 2/2003 | Mayshack et al. |

(Continued)

FOREIGN PATENT DOCUMENTS

EP    0299196 A2    1/1989    ............... F21M 1/00

OTHER PUBLICATIONS

Steris Surgical Solutions, HarmonyAIR® Equipment Columns and Supply Heads Product Brochure, Oct. 2016, pp. 1-8.

*Primary Examiner* — Bao Q Truong

(74) *Attorney, Agent, or Firm* — Kusner & Jaffe

(57) ABSTRACT

A lighthead identification system for controlling lightheads of a surgical lighting system. The lighthead identification system includes illuminated indicator lights that visually indicate to an operator that an associated lighthead has been selected for adjusting parameter settings on a user interface.

18 Claims, 6 Drawing Sheets

(56) References Cited

U.S. PATENT DOCUMENTS

| | | | |
|---|---|---|---|
| 6,601,985 B1 | 8/2003 | Jesurun et al. | |
| 6,655,817 B2 | 12/2003 | Devlin et al. | 362/233 |
| 7,394,367 B1* | 7/2008 | Aupperle | G05B 15/02 |
| | | | 340/530 |
| 8,273,076 B2 | 9/2012 | Devengenzo et al. | 606/1 |
| 8,308,333 B2 | 11/2012 | Fritze et al. | 362/572 |
| 8,526,033 B2 | 9/2013 | Kim | 358/1.15 |
| 9,119,240 B2 | 8/2015 | Nagazoe | |
| 2001/0030683 A1* | 10/2001 | Howell | E04B 9/006 |
| | | | 348/61 |
| 2002/0089857 A1* | 7/2002 | Borders | F21V 7/09 |
| | | | 362/399 |
| 2003/0142204 A1 | 7/2003 | Rus et al. | |
| 2003/0210559 A1 | 11/2003 | Jesurun et al. | |
| 2006/0016109 A1 | 1/2006 | Nicolaas | |
| 2009/0102396 A1 | 4/2009 | Petrucci et al. | |
| 2010/0049180 A1* | 2/2010 | Wells | A61N 5/0616 |
| | | | 606/12 |
| 2010/0325546 A1 | 12/2010 | Leo et al. | 715/719 |
| 2011/0128729 A1* | 6/2011 | Ng | B63B 45/04 |
| | | | 362/231 |
| 2012/0075832 A1 | 3/2012 | Schmid et al. | |
| 2013/0221183 A1* | 8/2013 | Volkenand | A61G 12/004 |
| | | | 248/550 |
| 2014/0062334 A1 | 3/2014 | Nagazoe et al. | 315/292 |
| 2015/0133960 A1 | 5/2015 | Lohmeier et al. | |
| | | | A61B 19/2203 |
| 2015/0317068 A1 | 11/2015 | Marka et al. | G06F 3/04842 |

* cited by examiner

LIGHTHEAD IDENTIFICATION SYSTEM FOR LIGHTHEAD CONTROL

RELATED APPLICATIONS

This application claims the benefit of U.S. Provisional Application No. 62/415,545, filed Nov. 1, 2016, and is hereby fully incorporated herein by reference.

FIELD OF THE INVENTION

The present invention relates generally to a control system for a surgical lighting system, and more particularly to a lighthead identification system for lighthead control.

BACKGROUND OF THE INVENTION

Surgical lighting systems are used in operating rooms to illuminate a work area (e.g., a surgical site). The surgical lighting systems include one or more lightheads that are typically mounted to a movable support structure (i.e., suspension system) comprised of one or more suspension arms for supporting lightheads and other lighting system accessory devices. Each lighthead includes a plurality of individual light sources (e.g., LED lighting modules or LED lighting pods). A control system (e.g., wall-mounted control system or an operating room integration (ORI) system) provides a means to independently adjust parameter settings (such as intensity, color temperature, focus, pattern size, and task/trim lighting) for each lighthead of the lighting system. A typical control system is comprised of a control unit having an associated user interface.

There are existing prior art lighting systems that have separate control units for controlling each lighthead of the lighting system, and existing prior art lighting systems that have a single master control unit for controlling a plurality of lightheads of a lighting system. In both embodiments, the control unit must be "mapped" to a respective lighthead in order for the operator to intuitively adjust the parameter settings for a particular lighthead. This "mapping" is commonly accomplished by applying adhesive stickers to each suspension arm supporting a lighthead, where each sticker functions as an identifier that correlates to an identifier shown on a user interface. For example, in a lighting system having four (4) lightheads, stickers (labeled with numbers 1-4) are applied to the respective suspension arms supporting the lightheads. The user interface shows a lighthead identifier (e.g., LH 1, LH 2, LH 3 and LH 4) that correlates or "maps" to the sticker numbers associated with the four lightheads. In this manner, a user can readily associate a particular lighthead with an adjustable parameter setting (e.g., light intensity).

Using stickers as indicators to "map" a lighthead to a parameter setting shown on a user interface has several drawbacks, including, but not limited to:

The readability of stickers is sensitive to the physical orientation of the suspension arms and distance from the user interface.

The mounting of stickers to a non-intuitive location on the suspension arm impedes immediate feedback to a user.

The stickers often become detached from suspension arms over time due to strong cleaning chemistries used to clean the suspension arms.

Stickers give the appearance of an inferior quality product.

If a lighting system does not have indicators associated with the lightheads, then there is no means for a user to readily correlate individual lightheads to lighthead parameter settings shown on the user interface. As a result, an operator needs to experiment by trial-and-error to associate lighthead parameter settings with a particular lighthead of the lighting system, thereby making the task of configuring the lighting system very time consuming.

The present invention provides a lighthead identification system that overcomes these and other drawbacks of the prior art.

SUMMARY OF THE INVENTION

In accordance with the present invention, there is provided a lighting system comprising: a support assembly; a plurality of lighting system accessory devices mounted to the support assembly; a control unit for controlling operation of the lighting system, said control unit including a user interface for adjusting parameter settings for the plurality of lighting system accessory devices; and a plurality of indicator lights, each indicator light associated with a respective lighting system accessory device, wherein the indicator lights visually indicate to a user that an associated lighting system accessory device has been selected at the user interface for adjusting a parameter setting for that lighting system accessory device.

An advantage of the present invention is the provision of a lighting system that provides immediate visual feedback to a user that a particular accessory device (e.g., lighthead) is selected for adjusting a respective parameter setting at a user interface.

Another advantage of the present invention is the provision of a lighting system that intuitively maps an accessory device (e.g., lighthead) to a user interface control for modifying parameter settings.

Still another advantage of the present invention is the provision of a lighting system that provides illuminated identification of each accessory device in a lighting system.

Yet another advantage of the present invention is the provision of a lighting system that allows a user to intuitively and readily understand which accessory device is being controlled at a user interface, without trial and error, or searching for a non-illuminated text-based indicator installed on a support assembly.

These and other advantages will become apparent from the following description of illustrated embodiments taken together with the accompanying drawings and the appended claims.

BRIEF DESCRIPTION OF THE DRAWINGS

The invention may take physical form in certain parts and arrangement of parts, embodiments of which will be described in detail in the specification and illustrated in the accompanying drawings which form a part hereof, and wherein.

DETAILED DESCRIPTION OF THE INVENTION

Figure 1:
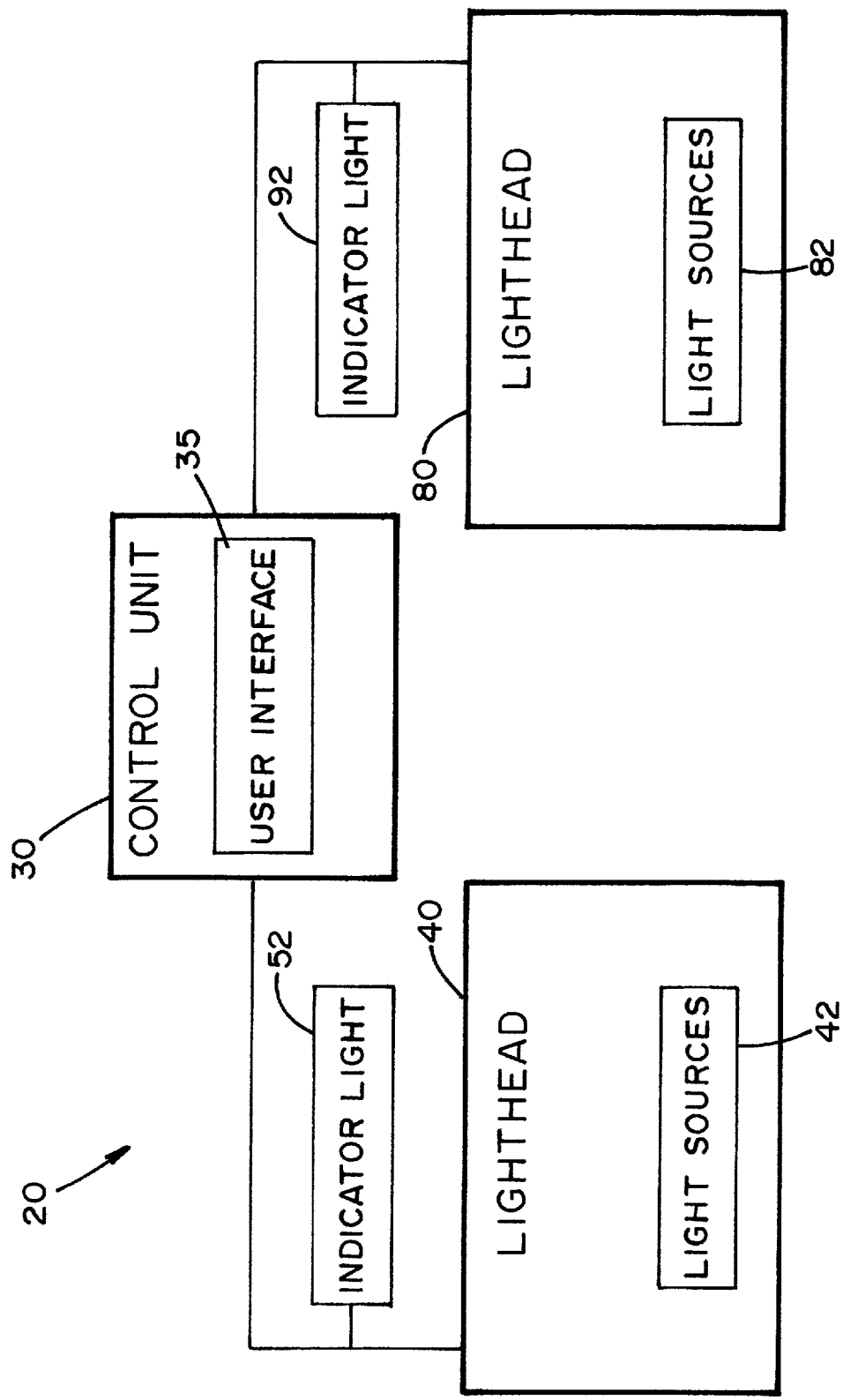
FIG. 1 is a block diagram of an example lighting system that includes a lighthead identification system according to an embodiment of the present invention.
Figure 2:
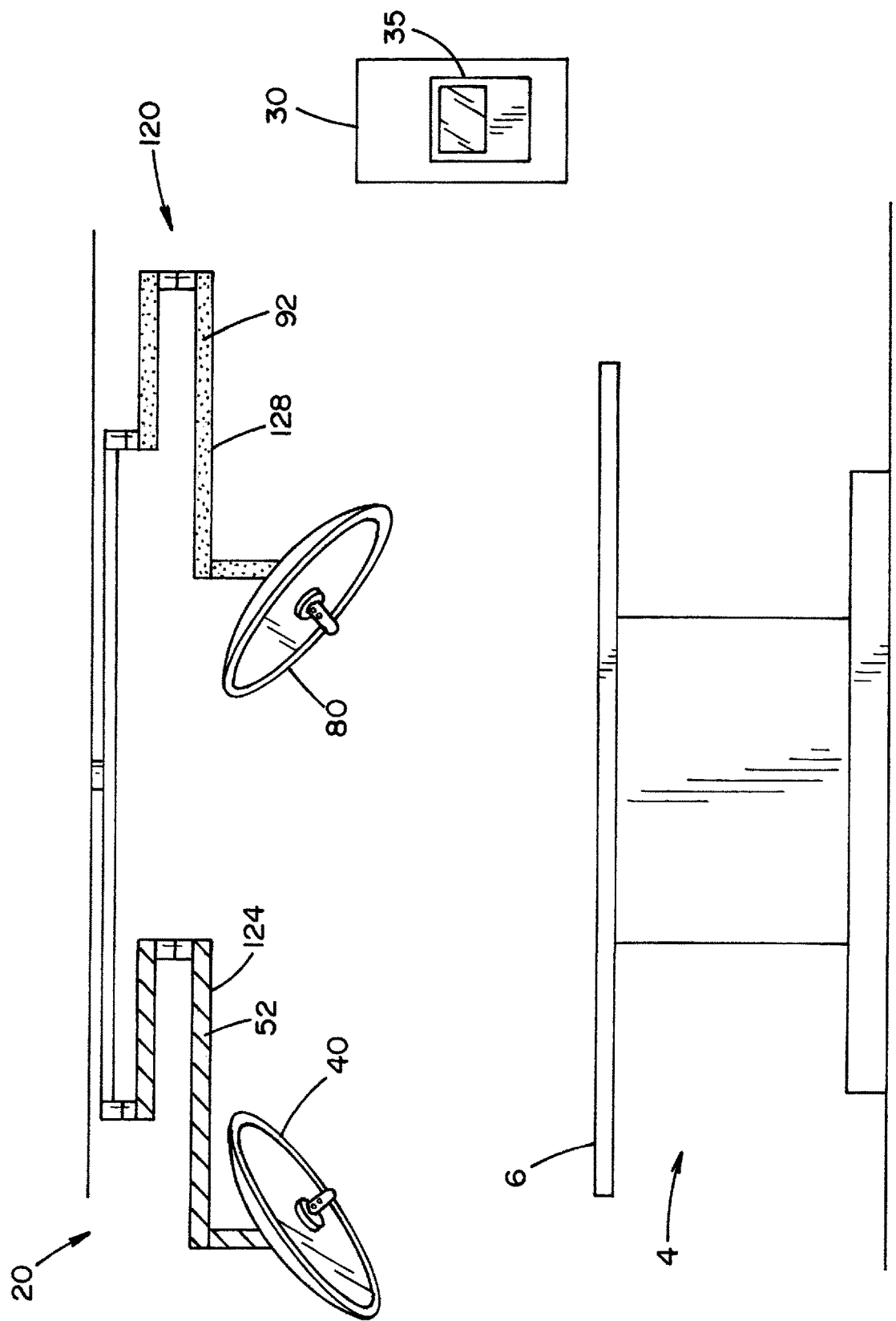
FIG. 2 is a schematic illustration of the lighting system shown in FIG. 1, wherein indicator lights are provided as illuminated trim on a suspension arm.

Referring now to the drawings wherein the showings are for the purposes of illustrating an embodiment of the invention only and not for the purposes of limiting same, FIG. 1 shows an example lighting system 20 that includes a lighthead identification system according to an embodiment of the present invention. FIG. 2 provides a schematic illustration of lighting system 20. In the illustrated embodiment, lighting system 20 is generally comprised of a control unit 30 having an associated user interface 35, one or more accessory devices, and indicator lights 52, 92 respectively associated with each accessory device. In the example lighting system 20, the accessory devices take the form of lightheads 40 and 80. Lighting system 20 also includes a support assembly for supporting the accessory devices above a surgical table 4 having a work surface 6. The support assembly may take the form of a conventional suspension system 120, as schematically shown in FIG. 2. As known to those skilled in the art, suspension system 120 is generally comprised of a plurality of suspension arms, hubs, mounts, yokes, and the like. Suspension system 120 is configured to allow repositioning of the accessory devices relative to work surface 6 of surgical table 4.

The example configuration of lighting system 20 of FIGS. 1 and 2 is shown solely for illustrating an embodiment of the present invention. In this regard, it should be appreciated that the present invention is intended for use with alternative configurations of lighting system 20. In this respect, lighting system 20 may also include various combinations of accessory devices mounted to the suspension system, including, but not limited to, lightheads, cameras, video cameras, video monitors, surgical lasers, and the like.

Control unit 30 is a conventional microprocessor-based computer system that is in communication with accessory devices, (e.g., lightheads 40, 80). User interface 35 may take the form of an interface device, including, but not limited to, a touchscreen, a control panel, a keypad, a remote control, a wall-mount control, and the like. User interface 35 may be a wired or wireless device.

In the illustrated embodiment, lighthead 40 is generally comprised of a plurality of light sources 42. Each light source 42 may take the form of an LED lighting module or an LED lighting pod. A respective light beam is produced by each light source 42.

Indicator light 52 is a component of the lighthead identification system of the present invention. Indicator light 52 includes one or more lighting elements, such as colored LEDs or other lighting devices. In the illustrated embodiment shown in FIG. 2, indicator light 52 is mounted in suspension arm 124 of suspension system 120 to serve as trim lighting.

Lighthead 80 is substantially the same as lighthead 40 described above. Lighthead 80 is generally comprised of a plurality of light sources 82. Each light source 82 may take the form of an LED lighting module or an LED lighting pod. A respective light beam is produced by each light source 82.

Indicator light 92 is a component of the lighthead identification system of the present invention. Indicator light 92 may take the same form as indicator light 52. In the embodiment illustrated in FIG. 2, indicator light 92 is mounted in suspension arms 128 of suspension system 120 as trim lighting.

Figure 3:
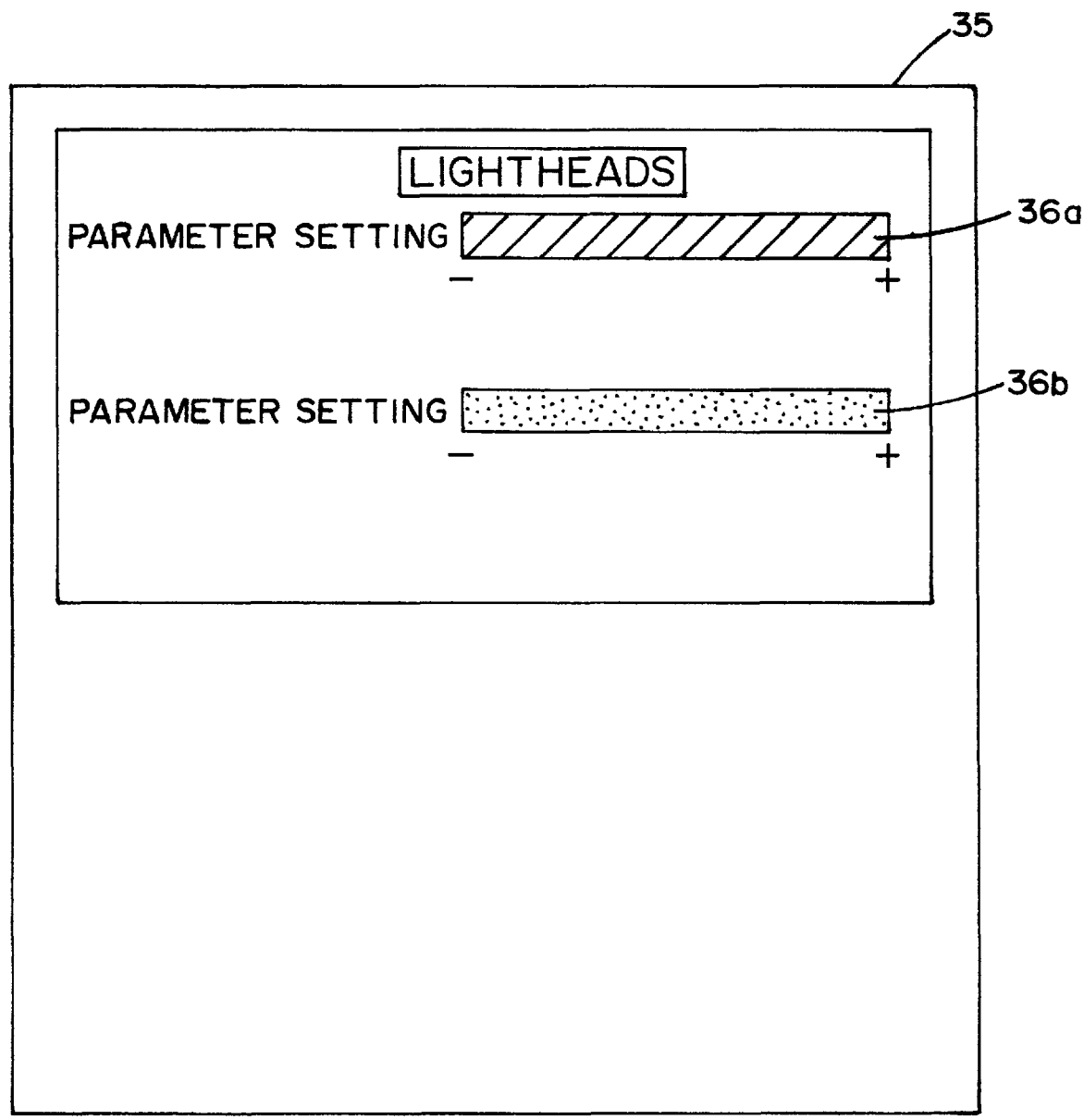
FIG. 3 illustrates a user interface for the lighting system that displays parameter settings for a plurality of lightheads, according to an embodiment of the present invention.

Referring now to FIG. 3, there is shown user interface 35 in the form of a touchscreen that displays respective parameter settings 36a, 36b for lightheads 40, 80. The example parameter settings 36a, 36b are light intensity. In accordance with the present invention, parameter setting 36a for lighthead 40 is displayed on user interface 35 in the same color as indicator light 52 (associated with lighthead 40), and parameter setting 36b for lighthead 80 is displayed on user interface 35 in the same color as indicator light 92 (associated with lighthead 80), where the color of indicator light 52 is different from the color of indicator light 92. It should be appreciated that the parameter settings may relate to any parameter associated with an accessory device that is adjustable via user interface 35, including, but not limited to, light intensity, color temperature, focus, pattern size, task/trim lighting, and the like.

The indicator lights of the present invention may have a plurality of operating states, wherein each operating state provides a different visual indicator to a user. For example, the different visual indicators may include, but are not limited to, different colors, different light intensities (e.g., dim/bright), light OFF, static light ON, flashing light, pulsing light, blinking light, and the like. The different operating states are used to indicate to a user which accessory device has been selected on the user interface 35 for modification to an accessory device parameter setting. In one embodiment of the present invention, the color, hue, or intensity of the indicator lights may be user-adjustable, via user interface 35, for customization of lighting system aesthetics.

In accordance with an example embodiment of the present invention, when a user displays lighthead parameter settings as shown in FIG. 3 and makes changes to parameter setting 36a, indicator light 52 associated with lighthead 40 is activated (e.g., illuminates or flashes), while indicator light 92 associated with lighthead 80 remains deactivated (OFF state). After a predetermined period of time, indicator light 52 is deactivated (OFF state). It is contemplated that the deactivated and activated states may take a variety of forms. For example, the deactivated state could be dim illumination while the activated state is a bright illumination. Alternatively, the deactivated state could be bright illumination, while the activated state is a pulsing mode or a color change. The deactivated and activated states of the indicator lights should be selected so that the user can easily perceive a visual differentiation between the two states.

The color coded display of parameter settings on user interface 35 in accordance with the present invention allows the amount of displayed text to be minimized while providing a user with correlation (i.e., mapping) between the parameter settings and the associated accessory device. As a result, display space on user interface 35 can be conserved, thereby avoiding crowding of icons or other display information.

In some user interfaces, a user may "swipe" or "tap" a touchscreen to select a particular accessory device, among a plurality of accessory devices, for modifying one or more respective parameter settings. As different accessory devices are selected, the indicator light associated with the selected accessory device is activated, while the indicator lights associated with other accessory devices are deactivated.

It should also be understood that the indicator lights of the present invention can also serve to indicate operating conditions of the lighting system. For example, the indicator lights can change states to indicate an operating condition, such as normal operating conditions, a fault condition, or an impending loss of operation (i.e., low battery power).

Figure 4:
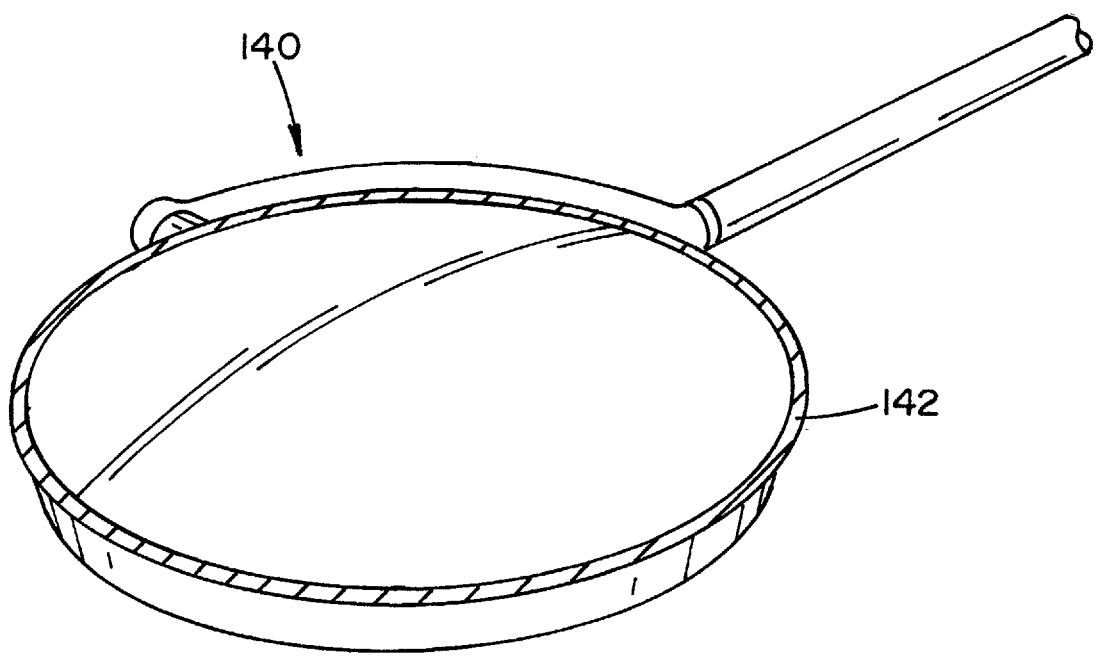
FIG. 4 illustrates an indicator light that is provided directly on a lighthead housing, according to an embodiment of the present invention.
Figure 5:
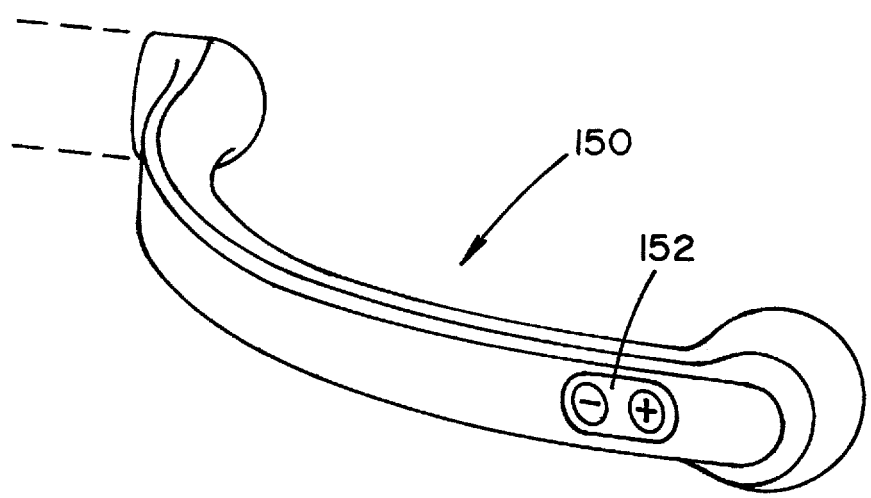
FIG. 5 illustrates an indicator light that is provided as a backlight for a control button on a yoke, according to an embodiment of the present invention.
Figure 6:
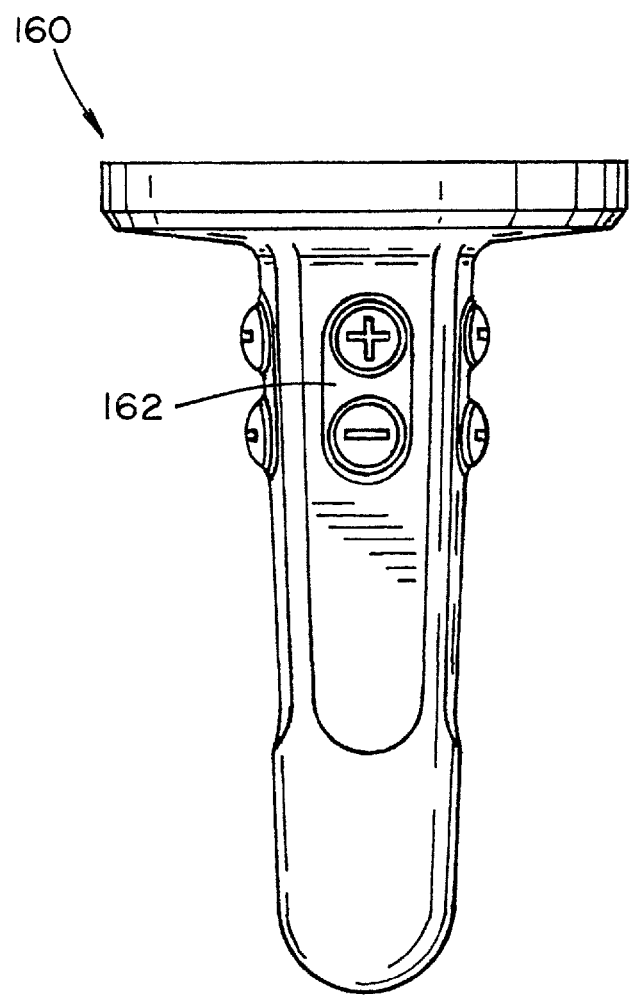
FIG. 6 illustrates an indicator light that is provided as a backlight for a control button on a handle for a lighthead, according to an embodiment of the present invention.

In an alternative embodiment of the present invention, an indicator light 142 is shown in FIG. 4 which is mounted within a housing for a lighthead 140 as accent trim lighting at the periphery of the housing for lighthead 140. It is also contemplated that the indicator light could take the form of an illuminated ring assembly comprising a ring-shaped housing and an annular arrangement of lighting elements, wherein the ring assembly is mounted to a lighthead housing. In another alternative embodiment of the present invention, an indicator light 152 is shown in FIG. 5 which is mounted within a yoke 150 (for supporting an accessory device) as a backlight for an accessory device control button. In still another alternative embodiment of the present invention, an indicator light 162 is shown in FIG. 6 that is mounted within a lighthead handle 160 as a backlight for a lighthead control button. It is also contemplated that the indicator light may be placed at other locations on a lighthead handle. For example, the indicator light may be integrated into the flange base portion of the lighthead handle or into the distal end portion of the lighthead handle. It should also be appreciated that the indicator light of the present invention may be located within (or attached to) other accessory devices or components of the lighting system that are not illustrated herein.

Figure 7:
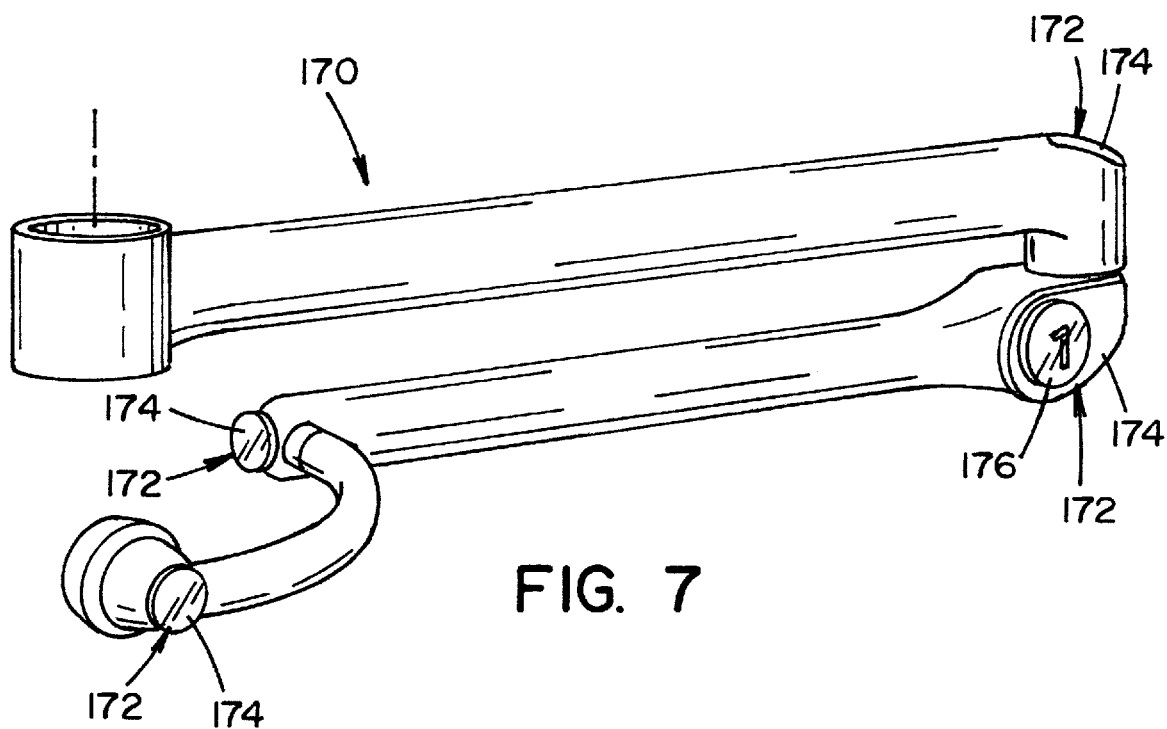
FIG. 7 illustrates indicator lights that are located on suspension arms of a suspension system, according to an embodiment of the present invention.
Figure 8:
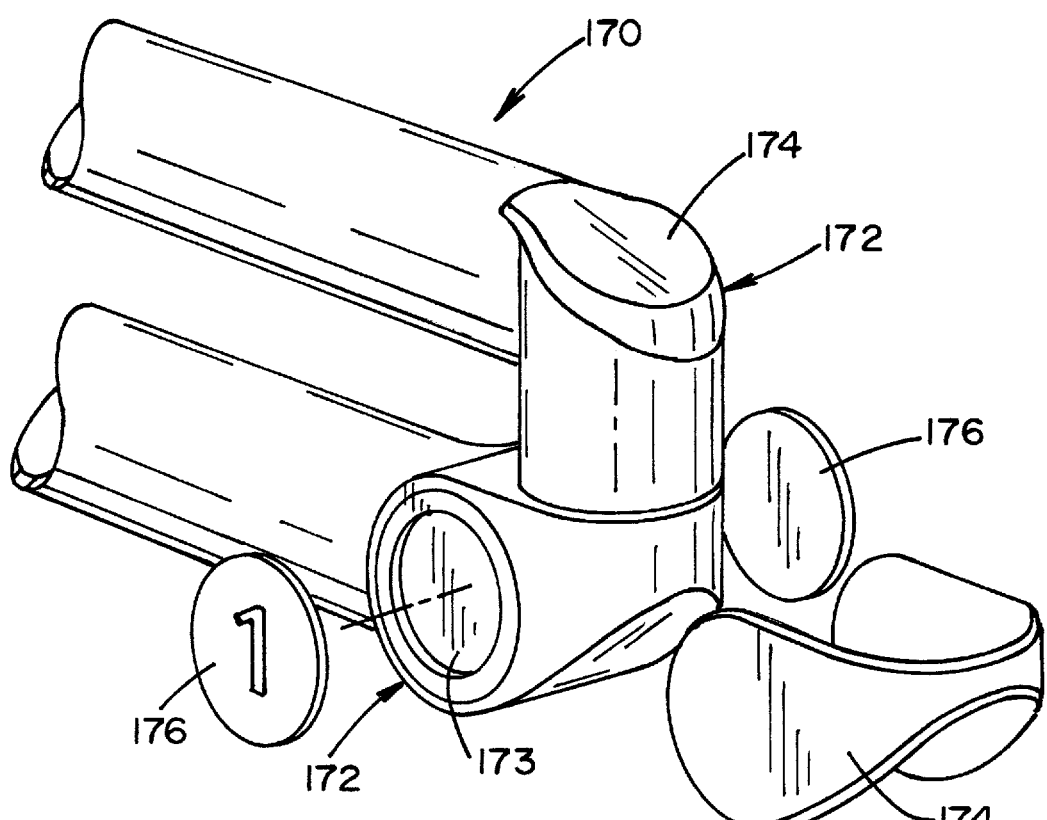
FIG. 8 illustrates an assembly for the indicator light shown in FIG. 7.

Referring now to FIGS. 7 and 8, there is shown a lighthead identification system according to an alternative embodiment of the present invention. In this embodiment, indicator lights 172 are located within arms 170 of a suspension system. For example, the indicator lights 172 may be located at joints that connect arms 170. Indicator lights 172 include one or more colored LEDs or other lighting elements 173 that are located within internal channels of arms 170. In the illustrated embodiment, indicator lights 172 also include an assembly comprising a translucent cap or cover 174. The assembly further comprises a punched or die cut label 176 that is applied over the translucent cap or cover 174. In one embodiment, the die cut label 176 displays a symbol, such as a number or letter which can be associated with an accessory device. An illuminated symbol improves the mapping of an accessory device to parameter settings displayed at user interface 35.

The foregoing describes specific embodiments of the present invention. It should be appreciated that these embodiments are described for purposes of illustration only, and that numerous alterations and modifications may be practiced by those skilled in the art without departing from the spirit and scope of the invention. It is intended that all such modifications and alterations be included insofar as they come within the scope of the invention as claimed or the equivalents thereof.

Having described the invention, the following is claimed:

1. A lighting system, comprising:
   a support assembly;
   a plurality of lighting system accessory devices mounted to the support assembly;
   a control unit for controlling operation of the lighting system, said control unit including a user interface for adjusting parameter settings for the plurality of lighting system accessory devices; and
   a plurality of indicator lights, each indicator light associated with a respective lighting system accessory device, wherein the indicator lights visually indicate to a user that an associated lighting system accessory device has been selected at the user interface for adjusting a parameter setting for that lighting system accessory device.

2. The lighting system of claim 1, wherein each indicator light has a different color.

3. The lighting system of claim 1, wherein the indicator lights have a plurality of operating states, wherein each operating state provides a different visual indicator to a user.

4. The lighting system of claim 3, wherein the visual indicators are selected from the group including: different colors, different light intensities, light OFF, static light ON, flashing light, pulsing light, and blinking light.

5. The lighting system of claim 3, wherein the plurality of operating states of the indicator lights include operating states that indicate operating conditions of the lighting system.

6. The lighting system of claim 1, wherein the indicator lights include one or more lighting elements.

7. The lighting system of claim 1, wherein at least one of the accessory devices is a surgical lighthead comprised of a plurality of light sources.

8. The lighting system of claim 7, wherein at least one of the indicator lights is mounted in a housing of the surgical lighthead or to a housing of the surgical lighthead.

9. The lighting system of claim 7, wherein at least one of the indicator lights is located in a handle of the surgical lighthead.

10. The lighting system of claim 1, wherein the accessory device is a surgical camera comprised of an imaging unit.

11. The lighting system of claim 1, wherein the accessory device is a video camera.

12. The lighting system of claim 1, wherein the accessory device is a surgical laser.

13. The lighting system of claim 1, wherein at least one of the indicator lights serves as trim lighting for the support assembly.

14. The lighting system of claim 1, wherein at least one of the indicator lights serves as a backlight for a control button.

15. The lighting system of claim 1, wherein at least one of the indicator lights is located at a joint between arms that form the suspension assembly.

16. The lighting system of claim 15, wherein the at least one indicator light includes an assembly comprised of a punched or die cut label that is applied over a translucent cover, said labels displaying a symbol.

17. The lighting system of claim 16, wherein the symbol is a number or letter that identifies an associated accessory device.

18. A lighting system, comprising:
   a support assembly;
   a plurality of lighting system accessory devices mounted to the support assembly;
   a control unit for controlling operation of the lighting system, said control unit including a user interface for adjusting parameter settings for the plurality of lighting system accessory devices; and
   a plurality of indicator lights, each indicator light associated with a respective lighting system accessory device, wherein the indicator lights visually indicate to a user that an associated lighting system accessory device has been selected at the user interface for adjusting a parameter setting for that lighting system accessory device;

wherein at least one of the indicator lights includes one or more lighting elements and an assembly comprised of a punched or die cut label that is applied over a translucent cover, said labels displaying a symbol.

\* \* \* \* \*